(12) United States Patent
Nakamura et al.

(10) Patent No.: US 8,323,625 B2
(45) Date of Patent: Dec. 4, 2012

(54) COCOON-SHAPED RUTILE-TYPE TITANIUM DIOXIDE, AS WELL AS COSMETICS AND EXTERNAL ADDITIVES FOR TONER COMPRISING THE SAME

(75) Inventors: Akira Nakamura, Yamaguchi (JP); Masayasu Morishita, Yamaguchi (JP); Hiromasa Kondoh, Yamaguchi (JP)

(73) Assignee: Titan Kogyo Kabushiki Kaisha, Yamaguchi (JP)

( * ) Notice: Subject to any disclaimer, the term of this patent is extended or adjusted under 35 U.S.C. 154(b) by 171 days.

(21) Appl. No.: 12/693,497

(22) Filed: Jan. 26, 2010

(65) Prior Publication Data

US 2010/0189666 A1    Jul. 29, 2010

(30) Foreign Application Priority Data

Jan. 27, 2009  (JP) ................................. 2009-015202

(51) Int. Cl.
*A61K 8/00*     (2006.01)
*B32B 5/16*     (2006.01)

(52) U.S. Cl. ......................................... 424/59; 428/402

(58) Field of Classification Search .................... 424/59; 428/402
See application file for complete search history.

(56) References Cited

U.S. PATENT DOCUMENTS 6,099,634 A * 8/2000 Uenishi et al. ................ 106/436
6,200,680 B1 * 3/2001 Takeda et al. ................. 428/402

* cited by examiner

*Primary Examiner* — Fereydoun G Sajjadi
*Assistant Examiner* — Genevieve S Alley
(74) *Attorney, Agent, or Firm* — McNees Wallace & Nurick LLC

(57) ABSTRACT

The present invention provides products comprising cocoon-shaped rutile-type titanium dioxide, i.e., cosmetics which have high UV blocking ability, provide a good feel upon use without leaving squeakiness or graininess on the skin, and also give a natural bare skin appearance without causing white masking, due to adequate tinting strength and covering power, as well as external additives for toner which are excellent in prevention of filming on a photosensitive member and inhibition of aggregation between toner particles. The present invention is directed to rutile-type titanium dioxide having a cocoon-shape, as well as cosmetics comprising this titanium dioxide, and external additives for toner comprising this titanium dioxide which is hydrophobically treated.

16 Claims, 2 Drawing Sheets

COCOON-SHAPED RUTILE-TYPE TITANIUM DIOXIDE, AS WELL AS COSMETICS AND EXTERNAL ADDITIVES FOR TONER COMPRISING THE SAME

RELATED APPLICATION

This application claims the benefits of Japanese Patent Application No. 2009-015202, filed on Jan. 27, 2009.

TECHNICAL FIELD

The present invention relates to cocoon-shaped rutile-type titanium dioxide having a specific size and shape, cosmetics comprising this titanium dioxide, and external additives for toner comprising this titanium dioxide which is hydrophobically treated.

The present invention particularly relates to cosmetics comprising the above titanium dioxide, which are smoothly applicable to the skin, leave no squeakiness or graininess on the skin, can give a natural bare skin appearance due to adequate hiding power and tinting strength, and also have high UV blocking ability.

BACKGROUND ART

With the recognition that UV light adversely affects the skin, make-up cosmetics with UV protection effect have also been developed, which comprise UV scatterers such as fine particulate titanium dioxide or fine particulate zinc oxide and/or organic UV absorbers. In recent years, there has been an increasing demand for cosmetics with high UV protection effect. In response to such a demand, it is usual to incorporate a high content of UV scatterers and/or UV absorbers. However, such a high content of UV scatterers (e.g., fine particulate titanium dioxide) in cosmetics leaves graininess on the skin or creates a thick cosmetic film, thereby resulting in an unnatural finish. On the other hand, such a high content of UV absorbers has a problem in safety, and in fact, it is not possible to use a high content of UV absorbers because there is a limit on their content to be incorporated. For these reasons, there is a strong demand for the development of a UV scatterer, particularly titanium dioxide, which has a high level of UV protection ability sufficient to ensure UV protection even at a low content.

Under these circumstances, the inventors of the present invention have proposed fan-shaped titanium dioxide composed of aggregated primary particles of needle-like titanium dioxide in Japanese Patent Public Disclosure No. H10-245228 (Patent Document 1). Since these particles were synthesized by the wet method to have a larger particle size, they had adequate hiding power and tinting strength, and also showed improved UV blocking ability, but not to satisfaction.

On the other hand, fine particulate-type titanium dioxide of 100 nm or less has been known as an external additive for toner since a long time ago. Although this type of titanium dioxide is excellent in imparting fluidity and controlling toner charge, it is feared that it would be embedded in the toner particle surface due to its small size, and therefore, it is not necessarily preferred for use as spacer particles for toner.

PRIOR ART DOCUMENT

Patent Document 1: Japanese Patent Public Disclosure No. H10-245228.

SUMMARY OF THE INVENTION

Problems to be Solved by the Invention

Thus, an object of the present invention is to provide titanium dioxide of a specific shape having greater UV blocking ability than conventional titanium dioxide, and cosmetics comprising this titanium dioxide. Cosmetics comprising the cocoon-shaped rutile-type titanium dioxide of the present invention leave no graininess and can provide a cosmetic film with a natural finish.

Another object of the present invention is to provide external additives for toner, which are not only preferred as spacer particles for toner, when compared to conventional fine particulate-type titanium dioxide used in external additives, but are also less likely to affect the color tone of toner due to its lower tinting strength than that of pigment-grade titanium dioxide synthesized by the calcination method.

Means for Solving the Problems

As a result of studies on the particle size and shape which achieve the maximum UV blocking ability in titanium dioxide, the inventors of the present invention have found that cocoon-shaped rutile-type titanium dioxide of a specific size, in which rod-shaped particles are aggregated into a cocoon shape, has greater UV blocking ability than conventional titanium dioxide. This finding led to the completion of the present invention.

Namely, the cocoon-shaped titanium dioxide of the present invention is rutile-type titanium dioxide having a specific surface area of 120 to 180 $m^2/g$ in the form of oriented and aggregated particles, in which the major axial planes of rod-shaped particles each having a minor axial diameter of 3 to 10 nm are oriented and aggregated in the minor axial direction, wherein the oriented and aggregated particles have an apparent mean major axial length of 80 to 300 nm, an apparent mean minor axial length of 30 to 150 nm, and an apparent mean axial ratio (apparent mean major axial length/apparent mean minor axial length) of 1.1 to 4, and wherein both major axial ends of the oriented and aggregated particles are round- or elliptical-shaped.

The particle surface of the above cocoon-shaped titanium dioxide may be coated with a layer containing one or more inorganic and organic materials.

The above inorganic material preferably comprises one or more members of aluminum, silicon, zinc, titanium, zirconium, iron, cerium and tin.

The above organic material preferably comprises one or more members of silicone-based compounds, various coupling agents and fatty acids.

It is also possible to obtain cosmetics comprising the above cocoon-shaped titanium dioxide.

It is also possible to obtain external additives for toner comprising the above cocoon-shaped titanium dioxide as a substrate.

Advantages of the Invention

The cocoon-shaped rutile-type titanium dioxide of the present invention is characterized by being more excellent in UV blocking ability than conventional rutile-type titanium dioxide, and by being less likely to cause white masking even when incorporated at a high content, due to its lower tinting strength than that of rutile-type titanium dioxide synthesized by the calcination method. Moreover, cosmetics comprising the cocoon-shaped rutile-type titanium dioxide of the present invention provide a good feel upon use without leaving squeakiness or graininess on the skin, and also have an effect of giving a natural bare skin appearance without causing white masking, due to adequate tinting strength and covering power.

Likewise, when used as an external additive for toner, the titanium dioxide of the present invention is preferred as spacer particles for toner in terms of the size of oriented and aggregated particles, although its effects of imparting fluidity and controlling toner charge are smaller than those of conventional fine particulate titanium dioxide for external additives. The titanium dioxide of the present invention is also less likely to affect the color tone of toner due to its lower tinting strength than that of titanium dioxide synthesized by the calcination method.

PREFERRED EMBODIMENT OF THE INVENTION

Figure 1:
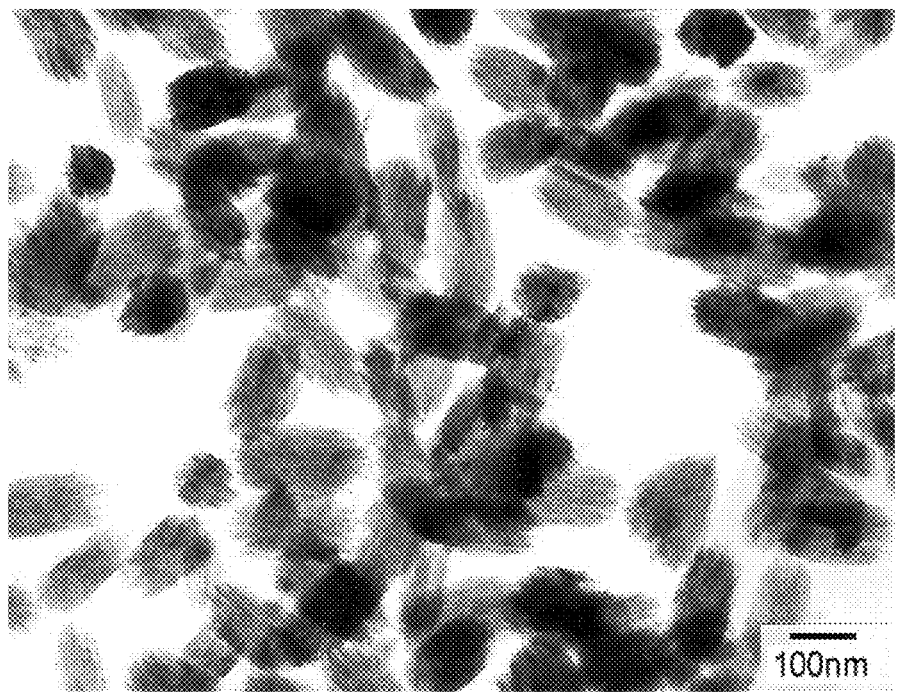
FIG. 1 is a transmission electron photomicrograph showing cocoon-shaped rutile-type titanium dioxide obtained in Preparation Example 1.

The titanium dioxide of the present invention will be further described in more detail below.

The cocoon-shaped rutile-type titanium dioxide of the present invention is rutile-type titanium dioxide having a specific surface area of 120 to 180 $m^2/g$ in the form of oriented and aggregated particles, in which the major axial planes of rod-shaped particles each having a minor axial diameter of 3 to 10 nm are oriented and aggregated in the minor axial direction, wherein the oriented and aggregated particles have an apparent mean major axial length of 80 to 300 nm, an apparent mean minor axial length of 30 to 150 nm, and an apparent mean axial ratio (apparent mean major axial length/apparent mean minor axial length) of 1.1 to 4, and wherein both major axial ends of the oriented and aggregated particles are round- or elliptical-shaped.

(Cocoon-shaped Particles)

Cocoon-shaped particles in the present invention refer to aggregates of particles with each constituent particle being rod-shaped, which are constructed such that the major axial planes of individual particles are three-dimensionally oriented in the minor axial direction. Such cocoon-shaped particles have a cylindrical shape, in which both major axial ends of oriented and aggregated particles are substantially round-shaped, i.e., are round- or elliptical-shaped. In contrast to conventional spindle particles having a smooth surface, these cocoon-shaped particles are characterized by having asperities on their surface because they are aggregates bound by the Van der Waals force between particles. For this reason, the cocoon-shaped particles of the present invention are characterized by having higher UV blocking ability than conventional fine particulate titanium dioxide, and provide high SPF (Sun Protection Factor) products when used in cosmetics.

(Apparent Mean Major Axial Length, Apparent Mean Minor Axial Length, and Apparent Mean Axial Ratio)

In the cocoon-shaped rutile-type titanium dioxide of the present invention, the apparent mean major axial length, apparent mean minor axial length and apparent mean axial ratio are mean values obtained from 70 aggregated particles, each of which is measured for its major axial length, minor axial length and axial ratio (major axial length/minor axial length) by transmission electron microscopy. As to the particle size dependency of light scattering and UV protection effects, the Mie theory (P. Stamatakis et al., J. Coatings Tech., 62(10), 95 (1990)) shows that a particle size of 30 to 60 nm provides the highest blocking effect at a wavelength of 300 nm, a particle size of 80 nm is most preferred at 350 nm, and a particle size of 120 nm is most preferred at 400 nm. The cocoon-shaped rutile-type titanium dioxide of the present invention preferably has an apparent mean major axial length of 100 to 200 nm, an apparent mean minor axial length of 60 to 100 nm, and an apparent mean axial ratio (apparent mean major axial length/apparent mean minor axial length) of 1.3 to 3.3. Particles having such properties are most preferred as source materials for high UV protection cosmetics because they have extremely high UV blocking ability when compared to conventional titanium dioxide. In a case where the oriented and aggregated particles have an apparent mean major axial length outside the range of 80 to 300 nm, an apparent mean minor axial length outside the range of 30 to 150 nm or an apparent mean axial ratio (apparent mean major axial length/apparent mean minor axial length) outside the range of 1.1 to 4, such particles are not preferred because their UV blocking ability is reduced.

(Specific Surface Area)

Specific surface area is measured by the BET method. Any specific surface area outside the above range is not preferred, because UV blocking ability is reduced and adequate tinting strength cannot be obtained.

(Surface Coating Layer)

To increase dispersion stability in a dispersion medium and durability during cosmetic production, the above cocoon-shaped rutile-type titanium dioxide preferably has an inorganic material coating over the aggregated particle surface. Examples of an inorganic material available for use include hydroxides or oxides of metals such as aluminum, silicon, zinc, titanium, zirconium, iron, cerium and tin. There is no limitation on the above metal salts used for this purpose. Moreover, such titanium dioxide is preferably subjected to water-repellent and/or oil-repellent treatment before being incorporated into cosmetics. Agents used for this treatment are organic materials including silicone compounds such as dimethylpolysiloxane and methylhydrogen polysiloxane, coupling agents of silane, aluminum, titanium and zirconium types, fluorine compounds such as perfluoroalkyl phosphate compounds, hydrocarbons, lecithin, amino acids, polyethylene, wax, as well as fatty acids such as lauric acid and stearic acid.

(Preparation Process)

A detailed explanation will be given below of how to prepare the cocoon-shaped rutile-type titanium dioxide of the present invention.

The cocoon-shaped rutile-type titanium dioxide of the present invention can be obtained by thermal hydrolysis of an acid-soluble titanium compound under HCl acidic conditions in the presence of an aliphatic hydroxy acid compound. Namely, in a case where rutile-type titanium dioxide is synthesized by thermal hydrolysis of an acid-soluble titanium compound with hydrochloric acid, when the hydrolysis is performed in the presence of an aliphatic hydroxy acid compound under specific conditions, the axial ratio becomes smaller than in conventional techniques, and rod-shaped fine particles are three-dimensionally aggregated to form size-controlled particles of a cocoon-shaped shape.

Hydrolysis conditions should be adjusted as appropriate for the acid solubility of an acid-soluble titanium compound, which is a source material. For example, in the case of using orthotitanic acid, which is obtained by alkali neutralization of a titanyl sulfate solution or a titanium tetrachloride solution, the $TiO_2$ concentration is adjusted to 50 to 140 g/L, preferably 60 to 120 g/L, the hydrochloric acid concentration is adjusted to 70 to 170 g/L, preferably 90 to 160 g/L, and the concentration of an aliphatic hydroxy acid compound is adjusted to 0.25 to 10 g/L, preferably 0.35 to 8.5 g/L, followed by hydrolysis at a temperature of 30° C. to 80° C., preferably 35° C. to 65° C.

(Acid-soluble Titanium Compound)

Any acid-soluble titanium compound may be used in the present invention as long as it is a titanium compound soluble in hydrochloric acid. Preferred is orthotitanic acid, which is obtained by alkali neutralization of titanyl sulfate or titanium tetrachloride at low temperature, but it is also possible to use an alkaline titanate, which is obtained from metatitanic acid by alkali treatment.

(Aliphatic Hydroxy Acid Compound)

Examples of an aliphatic hydroxy acid compound added in the present invention include, for example, glycolic acid, lactic acid, citric acid, tartaric acid, salicylic acid, malic acid, isocitric acid, and salts thereof, which may be used either alone or in combination. Preferred are citric acid compounds or isocitric acid compounds, which are preferably added in an amount of 0.5% to 7% by weight relative to $TiO_2$ contained in the acid-soluble titanium compound.

(Inorganic and Organic Pigments Available for Combined Use)

In the cosmetics of the present invention, various components used for normal cosmetics, including inorganic pigments and organic pigments, may be used in combination as needed. Examples of inorganic pigments available for combined use include titanium dioxide, zinc oxide, red iron oxide, yellow iron oxide, black iron oxide, ultramarine blue, iron blue, cerium oxide, talc, white mica, synthetic mica, bronze mica, black mica, synthetic fluorine bronze mica, titanated mica, micaceous iron oxide, sericite, zeolite, kaolin, bentonite, clay, silicic acid, silicic anhydride, magnesium silicate, magnesium aluminum silicate, calcium silicate, barium sulfate, magnesium sulfate, calcium sulfate, calcium carbonate, magnesium carbonate, boron nitride, bismuth oxychloride, alumina, zirconium dioxide, magnesium oxide, chromium oxide, calamine, hydroxyapatite, as well as composites thereof. Likewise, examples of organic pigments available for combined use include silicone powder, silicone elastic powder, polyurethane powder, cellulose powder, nylon powder, urethane powder, silk powder, PMMA powder, starch, polyethylene powder, polystyrene powder, carbon black, tar dye, natural dyes, and metal soaps such as zinc stearate, as well as composites thereof.

(Possible Other Components)

In addition to the above components, the cosmetics of the present invention may comprise other components depending on the intended purpose, within quantitative and qualitative ranges that do not impair the effect of the present invention. For example, the cosmetics of the present invention may further comprise, as appropriate, oil-based components, dyes, pH adjustors, moisturizers, thickeners, surfactants, dispersants, stabilizers, coloring agents, antiseptics, antioxidants, sequestering agents, astringents, antiphlogistics, UV absorbers, fragrances and so on, within the ranges that achieve the object of the present invention.

(Dosage Form of Cosmetics)

The cosmetics of the present invention can be prepared in a known manner, and may be formulated into any dosage form including powders, powder solids, creams, emulsions, lotions, oil-based liquids, oil-based solids, or pastes. For example, the cosmetics of the present invention may be provided in the form of make-up cosmetics such as make-up bases, foundations, concealers, face powders, control colors, sunscreen cosmetics, lipsticks, lip pomades, eyeshadows, eyeliners, mascaras, cheek colors, nail enamels, body powders, perfumed powders, or baby powders, as well as in the form of skin care cosmetics, hair care cosmetics, or the like.

(Content of Cocoon-shaped Rutile-type Titanium Dioxide)

The content of cocoon-shaped rutile-type titanium dioxide in these cosmetics may optionally be selected depending on properties required for each cosmetic, but it is 0.1% to 50% by weight, preferably 1% to 45% by weight, in order to ensure the characteristics of the present invention, i.e., smooth application to the skin, no squeakiness or graininess on the skin, and good UV protection ability when used in cosmetics. In contrast, a content exceeding 50% by weight is not preferable because it ensures good UV protection ability, but leaves strong squeakiness or graininess on the skin and gives an unnatural finish due to enhanced covering power.

In these cosmetics, the cocoon-shaped rutile-type titanium dioxide of the present invention may be used in combination with pigment-grade titanium dioxide and/or ultrafine particulate titanium dioxide, depending on the intended purpose.

The cocoon-shaped rutile-type titanium dioxide of the present invention can be used as a toner material and is particularly preferred as an external additive. Because of its size and particle form, the cocoon-shaped rutile-type titanium dioxide of the present invention is excellent in prevention of filming on a photosensitive member and inhibition of aggregation between toner particles, and it can be used for any mode of development, such as non-magnetic monocomponent development, magnetic monocomponent development, or bicomponent development.

EXAMPLES

The present invention will be further described in more detail by way of the following examples, which are provided for illustrative purposes only and are not intended to limit the scope of the invention.

Preparation Example 1

Synthesis of Cocoon-shaped Rutile-type Titanium Dioxide

Figure 2:
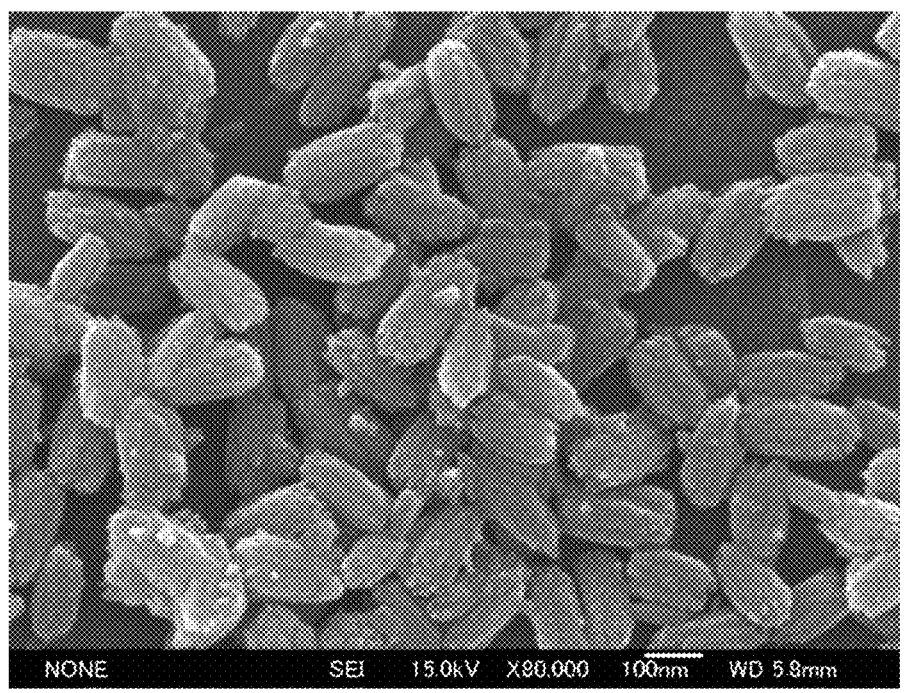
FIG. 2 is a scanning electron photomicrograph showing cocoon-shaped rutile-type titanium dioxide obtained in Preparation Example 1.

To a 160 g/L sodium carbonate solution, a titanyl sulfate solution was slowly added dropwise such that the solution temperature did not exceed 25° C. At the time point where the pH reached 10, the dropwise addition of the titanyl sulfate solution was stopped. A white precipitate of titanium hydroxide obtained in this neutralization step was filtered and washed well. Next, the washed o titanium hydroxide cake was repulped with dilute hydrochloric acid, followed by addition of concentrated hydrochloric acid and citric acid to give a $TiO_2$ concentration of 80 g/L, a hydrochloric acid concentration of 140 g/L and a citric acid concentration of 4.0 g/L. Subsequently, the solution temperature was elevated to 40° C. while stirring, and hydrolysis was performed at 40° C. for 20 hours under stirring conditions to synthesize rutile-type titanium dioxide. When observed under a transmission electron microscope, the resulting rutile-type titanium dioxide was found to be in the form of cylindrical cocoon-shaped particles having a mean major axial length of 105 nm, a mean minor axial length of 70 nm, a mean axial ratio of 1.5 and a specific surface area of 148 m²/g, in which rod-shaped particles were oriented and aggregated into a cocoon shape, as shown in FIG. 1. When the particle surface was observed under a scanning electron microscope, it was confirmed that rod-shaped particles were oriented and aggregated into a cocoon shape to thereby form cocoon-shaped particles, as shown in FIG. 2.

(Surface Treatment)

A water suspension containing the rutile-type titanium dioxide thus obtained was heated and adjusted to 70° C. Then, sodium aluminate was slowly added under stirring conditions in an amount of 10% (calculated as $Al_2O_3$) relative to the titanium dioxide. After stirring for 1 hour, dilute sulfuric acid was added to adjust the pH to 8.0. Next, sodium stearate was added in an amount of 5% relative to the titanium dioxide. After stirring for 1 hour, the pH was adjusted to 6.5 with dilute sulfuric acid. The suspension was filtered, washed and dried to give surface-treated rutile-type titanium dioxide.

Preparation Examples 2 to 6

The same procedure as shown in Preparation Example 1 was repeated to synthesize rutile-type titanium dioxide, except that the $TiO_2$ concentration, hydrochloric acid concentration, citric acid concentration and reaction temperature in Preparation Example 1 were changed as indicated in Table 1 to perform hydrolysis. When observed under a transmission electron microscope, the particles obtained in each case were confirmed to be cylindrical cocoon-shaped particles having the properties indicated in Table 1.

Comparative Preparation Example 1

Figure 3:
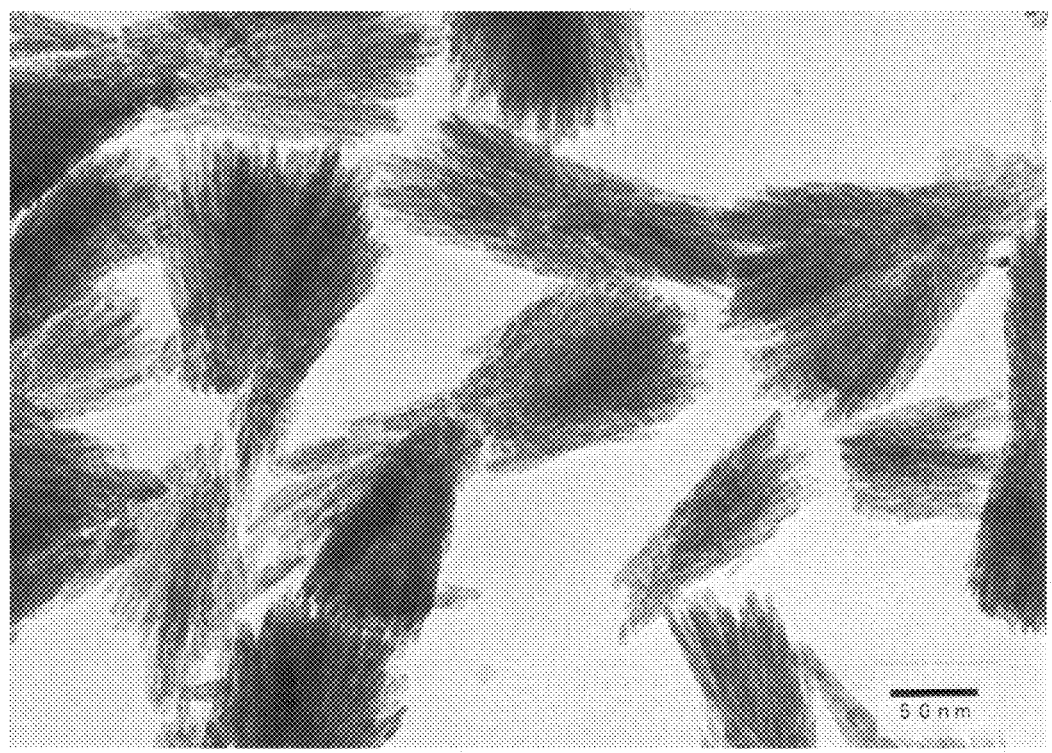
FIG. 3 is a transmission electron photomicrograph showing fan-shaped rutile-type titanium dioxide obtained in Comparative Preparation Example 1.

The same procedure as shown in Preparation Example 1 was repeated to synthesize rutile-type titanium dioxide, except that hydrolysis was performed in the absence of citric acid at a temperature of 60° C. When observed under a transmission electron microscope, the resulting rutile-type titanium dioxide was found to be in the form of fan-shaped particles having an edge length of 100 nm and a specific surface area of 160 m²/g, as shown in FIG. 3 (Sample G).

Comparative Preparation Example 2

A titanyl sulfate solution was decomposed by heating, filtered and washed to give a titanium dihydroxide oxide slurry. To this slurry, a caustic soda solution was added while stirring and heated at 95° C. for 2 hours. Then, this product was washed well, and hydrochloric acid was added to the resulting slurry while stirring to give a $TiO_2$ concentration of 90 g/L and a hydrochloric acid concentration of 50 g/L. Hydrolysis was performed by heating at 95° C. for 2 hours to synthesize rutile-type titanium dioxide. The resulting titanium dioxide was found to be in the form of spindle particles having a major axial length of 80 nm, a minor axial length of 15 nm and a specific surface area of 92 m²/g (Sample H).

Comparative Preparation Example 3

The spindle titanium dioxide obtained in Comparative Preparation Example 2 was adjusted to pH 7.0 at 80° C., filtered, washed with water, and dried at 105° C. This product was calcined in an electric furnace at 850° C. for 2 hours to give spherical rutile-type titanium dioxide having a mean particle size of 120 nm and a specific surface area of 14 m²/g (Sample I).

It should be noted that the rutile-type titanium dioxide synthesized in each comparative preparation example was subjected to the same surface treatment as used in Preparation Example 1 before being provided for comparison tests.

(Tinting Strength)

The surface-treated titanium dioxide (1.05 g) obtained in each preparation example or comparative preparation example, black iron oxide (0.03 g, BL-100, Titan Kogyo, Ltd., Japan) and dimethylpolysiloxane (2.00 g, 5000 cs) were weighed and dispersed by rotating at 75 rpm in a Hoover's muller with a load of 150 Lbs. The resulting paste was transferred to a 30 mmφ glass cell and measured for its L value with a SM-7 color computer (Suga Test Instruments Co., Ltd., Japan), which was used as an index of tinting strength. The results obtained are shown in Table 2.

TABLE 1

| Preparation Example | Hydrolysis conditions | | | | Properties of generated rutile-type titanium dioxide | | | |
|---|---|---|---|---|---|---|---|---|
| | $TiO_2$ conc. g/L | HCl conc. g/L | Citric acid conc. g/L | Temperature ° C. | Mean major axial length nm | Mean minor axial length nm | Mean axial ratio | Specific surface area m²/g |
| Preparation Example 1 (A) | 80 | 140 | 4.0 | 40 | 105 | 70 | 1.5 | 148 |
| Preparation Example 2 (B) | 60 | 160 | 3.0 | 35 | 166 | 113 | 1.5 | 165 |
| Preparation Example 3 (C) | 80 | 140 | 2.4 | 35 | 180 | 96 | 1.9 | 152 |
| Preparation Example 4 (D) | 80 | 140 | 2.4 | 40 | 129 | 59 | 2.3 | 141 |
| Preparation Example 5 (E) | 100 | 90 | 3.0 | 55 | 99 | 38 | 2.6 | 135 |
| Preparation Example 6 (F) | 60 | 160 | 1.8 | 35 | 229 | 122 | 1.9 | 170 |

TABLE 2

| Test sample | L value |
|---|---|
| Preparation Example 1 (A) | 56.6 |
| Preparation Example 2 (B) | 64.7 |
| Preparation Example 3 (C) | 66.7 |
| Preparation Example 4 (D) | 58.9 |
| Preparation Example 5 (E) | 49.4 |
| Preparation Example 6 (F) | 66.7 |
| Comparative Preparation Example 1 (G) | 66.2 |
| Comparative Preparation Example 2 (H) | 35.1 |
| Comparative Preparation Example 3 (I) | 71.1 |

As shown in Table 2, the L value, which was used as an index of tinting strength, was smaller in the cocoon-shaped rutile-type titanium dioxide of the present invention than in the spherical titanium dioxide of Comparative Preparation Example 3 synthesized by the calcination method.

Examples 1 to 6 and Comparative Examples 1 to 3

W/O Liquid Foundation

The cocoon-shaped rutile-type titanium dioxide particles (A to F) obtained in Preparation Examples 1 to 6 and the rutile-type titanium dioxide particles obtained in Comparative Preparation Examples 1 to 3 were used to prepare W/O liquid foundations according to the formulation shown below.

| (Components) | Weight (%) |
|---|---|
| 1. Crosslinked polyether-modified silicone*[1] | 4.0 |
| 2. Crosslinked dimethylpolysiloxane*[2] | 6.0 |
| 3. Branched polyether-modified silicone*[3] | 2.0 |
| 4. Decamethylcyclopentasiloxane | 21.0 |
| 5. Dimethylpolysiloxane (6 mm$^2$/second (25° C.)) | 7.0 |
| 6. Surface-treated titanium dioxide obtained in each preparation example or comparative preparation example | 15.0 |
| 7. Silicone-treated talc | 4.0 |
| 8. Silicone-treated coloring material | 1.5 |
| 9. 1,3-Butylene glycol | 5.0 |
| 10. Sodium citrate | 0.4 |
| 11. Sodium chloride | 0.5 |

-continued

| (Components) | Weight (%) |
|---|---|
| 12. Antiseptic | q.s. |
| 13. Purified water | balance |

*[1]KSG-210 (Shin-Etsu Chemical Co., Ltd., Japan)
*[2]KSG-15 (Shin-Etsu Chemical Co., Ltd., Japan)
*[3]KF-6028 (Shin-Etsu Chemical Co., Ltd., Japan)

(Preparation Process)
A: Components 6 to 8 were uniformly mixed together.
B: Components 1 to 5 were uniformly mixed together, and A was uniformly dispersed therein.
C: Components 9 to 13 were uniformly mixed together.
D: Under stirring conditions, C was slowly added and emulsified in B to give a W/O liquid foundation.

[Evaluation Items and Evaluation Method for Assessing Cosmetics]

(UV Blocking Ability)

The W/O liquid foundations thus prepared were each applied onto a transpore tape at 2 mg/cm$^2$, and then measured for SPF with a Labsphere UV-1000S SPF analyzer.

The SPF data measured are shown in Table 3.

TABLE 3

| Test sample | SPF (in vitro) |
|---|---|
| Example 1 (A) | 36 |
| Example 2 (B) | 30 |
| Example 3 (C) | 36 |
| Example 4 (D) | 39 |
| Example 5 (E) | 24 |
| Example 6 (F) | 28 |
| Comparative Example 1 (G) | 26 |
| Comparative Example 2 (H) | 20 |
| Comparative Example 3 (I) | 23 |

As can be seen from Table 3, the cocoon-shaped rutile-type titanium dioxide of the present invention had a higher SPF and hence was more excellent in UV blocking ability than conventional spindle titanium dioxide, fan-shaped titanium dioxide and calcined titanium dioxide.

(Sensory Test)

The W/O liquid foundations prepared above were subjected to a sensory test to evaluate their spreadability, smoothness, skin clarity, color after application, covering power and so on. The results obtained are shown in Table 4.

TABLE 4

| Test sample | Spreadability | Smoothness | Graininess | Skin clarity | Covering power | White masking | Long-lasting quality |
|---|---|---|---|---|---|---|---|
| Example 1 (A) | + | + | + | ++ | + | ++ | ++ |
| Example 2 (B) | + | ++ | + | + | + | + | ++ |
| Example 3 (C) | ++ | ++ | ++ | + | + | + | + |
| Example 4 (D) | + | + | + | ++ | + | ++ | ++ |
| Example 5 (E) | + | + | + | ++ | +/− | + | ++ |
| Example 6 (F) | ++ | + | + | + | ++ | +/− | + |
| Comparative Example 1 (G) | +/− | +/− | +/− | + | ++ | + | + |
| Comparative Example 2 (H) | − | − | +/− | ++ | − | ++ | +/− |
| Comparative Example 3 (I) | − | − | − | − | ++ | − | +/− |

[Evaluation and Evaluation Criteria]

The W/O liquid foundations prepared in Examples 1 to 6 and Comparative Examples 1 to 3 were used by 10 panelists and evaluated for the sensory test items indicated in Table 4 on a five-point scale. The results were averaged for assessment.

(Evaluation Criteria)

Very good=5; Good=4; Fair=3; Slightly poor=2; and Poor=1

(Assessment Criteria)

Averaged score of 4.0 to 5.0=++; 3.0 to less than 4.0=+; 2.0 to less than 3.0=+/−; and 1.0 to less than 2.0=−

As a result of the sensory test, all of the foundations obtained in Examples 1 to 6 according to the present invention were more excellent in spreadability and smoothness upon application than those of Comparative Examples 1 to 3, and were also excellent in skin clarity after application and gave a natural finish with a bare skin appearance due to adequate covering power without causing white masking. Moreover, the foundations of the present invention were also good in long-lasting quality and maintained the bare skin appearance. In this way, upon incorporation of cocoon-shaped aggregated particles of rutile-type titanium dioxide having a specific surface area of 120 to 180 m$^2$/g, which are formed by aggregation of rod-shaped particles into a cocoon shape and whose particle size observed under a transmission electron microscope is 80 to 300 nm for mean major axial length and 30 to 150 nm for apparent mean minor axial length with an apparent mean axial ratio of 1.1 to 4, wherein both major axial ends of the oriented and aggregated particles are round- or elliptical-shaped, it is possible to provide cosmetics which are smoothly applicable to the skin, leave no squeakiness or graininess on the skin, and give a natural bare skin appearance due to adequate tinting strength and covering power.

Example 7

Powder Foundation

| (Components) | Weight (%) |
|---|---|
| 1. Caprylylsilane-treated mica*[1] | 40.0 |
| 2. Powder of Preparation Example 3 | 5.0 |
| 3. Silicone-treated talc*[2] | balance |
| 4. Silicone-treated pigment-grade titanium dioxide*[2] | 5.0 |
| 5. Silicone-treated fine particulate titanium dioxide*[2] | 5.0 |
| 6. Silicone-treated barium sulfate*[2] | 10.0 |
| 7. Silicone-treated red iron oxide*[2] | 0.4 |
| 8. Silicone-treated yellow iron oxide*[2] | 2.0 |
| 9. Silicone-treated umber*[2] | 0.4 |
| 10. Silicone-treated black iron oxide*[2] | 0.1 |
| 11. Phenyl-modified hybrid silicone composite powder*[3] | 2.0 |
| 12. Spherical polymethylsilsesquioxane powder*[4] | 0.5 |
| 13. Antiseptic | q.s. |
| 14. Fragrance | q.s. |
| 15. Crosslinked dimethylpolysiloxane*[5] | 4.0 |
| 16. Glyceryl trioctanoate | 2.0 |
| 17. Squalane | 1.0 |

*[1] treated with AES-3083 (Shin-Etsu Chemical Co., Ltd., Japan)
*[2] treated with KF-9909 (Shin-Etsu Chemical Co., Ltd., Japan)
*[3] KSP-300 (Shin-Etsu Chemical Co., Ltd., Japan)
*[4] KMP-590 (Shin-Etsu Chemical Co., Ltd., Japan)
*[5] KSG-16 (Shin-Etsu Chemical Co., Ltd., Japan)

(Preparation Process)
A: Components 1 to 13 were mixed together and uniformly pulverized.
B: Components 15 to 17 were uniformly mixed together and added to A in a uniform state.
C: Component 14 was added to B, followed by press molding in a mold to give a powder foundation.

The resulting powder foundation was smoothly and lightly spreadable, excellent in adhesion to the skin, satisfactorily maintained on the skin, free from stickiness, resistant to sweat or the like, excellent in long-lasting quality, and also excellent in feel upon use and usability.

Example 8

Pressed Powder

| (Components) | Weight (%) |
|---|---|
| 1. Talc | balance |
| 2. PMMA (7 μm)*[1] | 10.0 |
| 3. Sericite | 30.0 |
| 4. Silica flake*[2] | 3.0 |
| 5. Powder of Preparation Example 5 | 6.0 |
| 6. Antiseptic | q.s. |
| 7. Coloring material | q.s. |
| 8. Octyl methoxycinnamate | 3.0 |
| 9. Squalane | 2.0 |
| 10. Antiseptic | q.s. |
| 11. Antioxidant | q.s. |
| 12. Fragrance | q.s. |

*[1] Matsumoto Microsphere M-100 (Matsumoto Yushi-Seiyaku Co., Ltd., Japan)
*[2] Sunlovely C (Dokai Chemical Industries, Japan)

(Preparation Process)
A: Components 1 to 7 were mixed together and pulverized.
B: A was transferred to a Henschel mixer, and Components 8 to 12 were added thereto, followed by stirring and mixing to a uniform state.
C: B was pulverized with an atomizer and press-molded in an aluminum dish to give a pressed powder.

The resulting pressed powder was confirmed to be excellent in spreadability and smoothness upon application and also maintain a natural finish even after application.

Example 9

Two-way Cake Foundation

| (Components) | Weight (%) |
|---|---|
| 1. Methicone-treated talc | balance |
| 2. Powder of Preparation Example 4 | 10.0 |
| 3. Methicone-treated mica | 20.0 |
| 4. Methicone-treated sericite | 36.0 |
| 5. Nylon powder | 10.0 |
| 6. Methicone-treated yellow iron oxide | 1.0 |
| 7. Methicone-treated red iron oxide | 0.5 |
| 8. Methicone-treated black iron oxide | 0.1 |
| 9. Dimethylpolysiloxane 1000 cs | 6.0 |
| 10. Isotridecyl isononanoate | 3.0 |
| 11. Squalane | 3.0 |
| 12. Antiseptic | 0.2 |
| 13. Antioxidant | 0.1 |

(Preparation Process)
A: Components 9 to 13 were dissolved by heating.
B: Components 1 to 8 were mixed together in a Henschel mixer, and then mixed with A.
C: B was pulverized with an atomizer and press-molded in an aluminum dish to give a two-way cake foundation.

The resulting two-way cake foundation was confirmed to be excellent in spreadability and smoothness upon application, and also be excellent in skin clarity after application to thereby give a natural finish with a bare skin appearance due to adequate covering power without causing white masking.

Example 10

Oil-based Cake Foundation

| (Components) | Weight (%) |
|---|---|
| 1. Dimethicone-treated talc | 5.3 |
| 2. Powder of Preparation Example 1 | 15.0 |
| 3. Dimethicone-treated sericite | 28.2 |
| 4. Dimethicone-treated red iron oxide | 0.5 |
| 5. Dimethicone-treated yellow iron oxide | 1.8 |
| 6. Dimethicone-treated black iron oxide | 0.2 |
| 7. Candelilla wax | 1.0 |
| 8. Carnauba wax | 1.0 |
| 9. Ceresin | 1.5 |
| 10. Decamethylcyclopentasiloxane | 14.0 |
| 11. Isononyl isononanoate | balance |
| 12. Polyglyceryl diisostearate | 2.0 |
| 13. Dextrin palmitate | 1.0 |
| 14. Octyl methoxycinnamate | 3.0 |
| 15. Antiseptic | q.s. |
| 16. Antioxidant | q.s. |

(Preparation Process)

A: Components 1 to 6 were mixed together in a Henschel mixer and uniformly pulverized.

B: Components 8 to 16 were dissolved by heating, to which A was then added and stirred to a uniform state.

C: After defoaming, the bulk was poured into a tray and slowly cooled to room temperature to give an oil-based cake foundation.

The resulting oil-based cake foundation was confirmed to be excellent in spreadability and smoothness upon application, and also be excellent in skin clarity after application to thereby give a natural finish with a bare skin appearance due to adequate covering power without causing white masking.

Example 11

Stick Foundation

| (Components) | Weight (%) |
|---|---|
| 1. Dimethylpolysiloxane | 18.0 |
| 2. Decamethylcyclopentasiloxane | 30.0 |
| 3. Octyl methoxycinnamate | 5.0 |
| 4. Diisostearyl malate | 4.0 |
| 5. Candelilla wax | 6.0 |
| 6. Hydrogenated jojoba ester | 4.0 |
| 7. Cetyl dimethicone copolyol | 2.0 |
| 8. Sorbitan sesquiisostearate | 0.5 |
| 9. Antioxidant | q.s. |
| 10. Antiseptic | q.s. |
| 11. Fragrance | q.s. |
| 12. Methicone-treated coloring material | 0.5 |
| 13. Powder of Preparation Example 2 | 8.5 |
| 14. Methicone-treated talc | 6.0 |
| 15. Methicone-treated mica | 2.0 |
| 16. Polymethyl methacrylate | 2.0 |
| 17. Purified water | balance |
| 18. Sodium citrate | 0.3 |
| 19. 1,3-Butylene glycol | 3.0 |
| 20. Glycerine | 2.0 |
| 21. Antiseptic | q.s. |

(Preparation Process)

A: Components 12 to 16 were mixed together in a Henschel mixer.

B: In a container large enough to hold all components, Components 1 to 11 were weighed and dissolved by heating.

C: In another container, Components 17 to 21 were weighed and dissolved by heating.

D: A was added and uniformly dispersed in B, and C was then emulsified therein.

E: After defoaming, the bulk was poured into a mold and slowly cooled to room temperature to give a stick foundation.

The resulting stick foundation was confirmed to be excellent in spreadability and smoothness upon application, and also be excellent in skin clarity after application to thereby give a natural finish with a bare skin appearance due to adequate covering power without causing white masking.

Example 12

W/O Emulsion Foundation

| (Components) | Weight (%) |
|---|---|
| 1. POE-modified silicone (HLB = 4.5) | 0.8 |
| 2. Polyglyceryl polyricinoleate | 0.5 |
| 3. Neopentyl glycol dicaprate | 3.0 |
| 4. Squalane | 1.0 |
| 5. Pentaerythrityl tetraoctanoate | 2.0 |
| 6. Stearoyl inulin*[1] | 1.0 |
| 7. Octyl methoxycinnamate | 4.0 |
| 8. Cyclomethicone | 15.4 |
| 9. Antiseptic | q.s. |
| 10. Antioxidant | q.s. |
| 11. Fragrance | q.s. |
| 12. Powder of Preparation Example 6 | 8.0 |
| 13. Silicon-treated talc | 5.7 |
| 14. Silicon-treated coloring material | 1.0 |
| 15. Purified water | balance |
| 16. 1,3-Butylene glycol | 6.0 |
| 17. Glycerine | 1.0 |
| 18. Sodium chloride | 1.0 |
| 19. Antiseptic | q.s. |

*[1] Rheopearl ISK (Chiba Flour Milling, Japan)

(Preparation Process)

A: Components 12 to 14 were stirred and mixed together in a Henschel mixer.

B: To Components 1 to 11, A was added and uniformly dispersed with a stirrer.

C: In another container, Components 15 to 19 were dissolved by heating.

D: C was added and emulsified in B, and then cooled to room temperature to give a W/O emulsion foundation.

The resulting W/O emulsion foundation was confirmed to be excellent in spreadability and smoothness upon application, and also be excellent in skin clarity after application to thereby give a natural finish with a bare skin appearance due to adequate covering power without causing white masking.

Example 13

O/W Emulsion Foundation

| (Components) | Weight (%) |
| --- | --- |
| 1. Stearic acid | 0.4 |
| 2. Isostearic acid | 0.3 |
| 3. Cetyl 2-ethylhexanoate | 4.0 |
| 4. Liquid paraffin | 11.0 |
| 5. POE(10)stearyl ether | 2.0 |
| 6. Cetyl alcohol | 0.3 |
| 7. Antiseptic | 0.2 |
| 8. Talc | 15.0 |
| 9. Coloring material | 4.0 |
| 10. Powder of Preparation Example 2 | 3.0 |
| 11. Triethanolamine | 0.4 |
| 12. Propylene glycol | 5.0 |
| 13. Purified water | 54.1 |
| 14. Antiseptic | 0.2 |
| 15. Antioxidant | 0.1 |

(Preparation Process)
A: Components 1 to 7 were dissolved by heating at 85° C.
B: Components 8 to 10 were mixed together and pulverized.
C: Components 11 to 15 were dissolved and mixed together by heating at 85° C.
D: B was added and uniformly dispersed in A, to which C was then slowly added and emulsified, followed by cooling to room temperature under stirring conditions. The emulsion was then filled into an appropriate container to give an O/W emulsion foundation.

The resulting O/W emulsion foundation was confirmed to be excellent in spreadability and smoothness upon application, and also be excellent in skin clarity after application to thereby give a natural finish with a bare skin appearance due to adequate covering power without causing white masking.

Example 14

O/W Moisturizing Cream

| (Components) | Weight (%) |
| --- | --- |
| 1. Crosslinked dimethylpolysiloxane*[1] | 8.0 |
| 2. Crosslinked dimethylpolysiloxane*[2] | 28.0 |
| 3. Decamethylcyclopentasiloxane | 10.0 |
| 4. Powder of Preparation Example 1 | 5.0 |
| 5. Branched polyglycerine-modified silicone*[3] | 0.3 |
| 6. Branched polyglycerine-modified silicone*[4] | 0.6 |
| 7. (Acrylamide/acryloyldimethyltaurine Na)copolymer*[5] | 0.6 |
| 8. Ammonium acryloyldimethyltaurate/VP copolymer (5% aqueous solution)*[6] | 12.0 |
| 9. Polyethylene glycol 400 | 1.0 |
| 10. Sodium lactate | 5.0 |
| 11. 1,3-Butylene glycol | 5.0 |
| 12. Purified water | 24.5 |

*[1]KSG-15 (Shin-Etsu Chemical Co., Ltd., Japan)
*[2]KSG-16 (Shin-Etsu Chemical Co., Ltd., Japan)
*[3]KF-6104 (Shin-Etsu Chemical Co., Ltd., Japan)
*[4]KF-6100 (Shin-Etsu Chemical Co., Ltd., Japan)
*[5]Simulgel 600 (Seppic)
*[6]Aristoflex AVC (Clariant)

(Preparation Process)
A: Components 3 to 5 were mixed together and uniformly dispersed.
B: Components 1 and 2 and A were uniformly mixed together.
C: Components 6 to 12 were uniformly mixed together.
D: Under stirring conditions, B was slowly added and emulsified in C to give an O/W moisturizing cream.

The resulting O/W moisturizing cream was confirmed to have a silky touch without stickiness or unctuousness, be lightly spreadable, leave no squeakiness, give a light and refreshing feel upon use, and remain moist and fresh, be free from temperature- or time-induced changes, and also be very excellent in usability and stability.

Example 15

O/W Cream

| (Components) | Weight (%) |
| --- | --- |
| 1. Crosslinked dimethylpolysiloxane*[1] | 5.0 |
| 2. Powder of Preparation Example 3 | 1.0 |
| 3. Glyceryl triisostearate | 8.0 |
| 4. Cetanol | 0.5 |
| 5. Stearic acid | 1.0 |
| 6. Glyceryl monostearate | 0.5 |
| 7. Sorbitan sesquioleate | 0.5 |
| 8. Polyoxyethylene sorbitan monooleate | 1.0 |
| 9. Triethanolamine | 0.5 |
| 10. Carbomer (1% aqueous solution) | 20.0 |
| 11. Locust bean gum (2% aqueous solution) | 5.0 |
| 12. 1,3-Butylene glycol | 7.0 |
| 13. Antiseptic | q.s. |
| 14. Fragrance | q.s. |
| 15. Purified water | 50.0 |

*[1]KSG-15 (Shin-Etsu Chemical Co., Ltd., Japan)

(Preparation Process)
A: Components 1 to 8 were mixed together by heating to a uniform state.
B: Components 9 to 13 and 15 were mixed together and heated.
C: Under stirring conditions, B was slowly added and emulsified in A, and after cooling, Component 14 was added thereto to give an O/W cream.

The resulting O/W cream was confirmed to have a silky touch without stickiness or unctuousness, be lightly spreadable, be excellent in tight adhesion to the skin, be satisfactorily maintained on the skin, give a light and refreshing feel upon use, and remain moist and fresh, be free from temperature- or time-induced changes, and also be very excellent in usability and stability.

Example 16

W/O Cream

| (Components) | Weight (%) |
| --- | --- |
| 1. Crosslinked alkyl/polyether-modified silicone*[1] | 3.0 |
| 2. Crosslinked alkyl-modified dimethylpolysiloxane*[2] | 4.0 |
| 3. Alkyl-modified branched polyether-modified silicone*[3] | 1.0 |
| 4. Meadowfoam oil | 3.5 |
| 5. Macadamia nut oil | 5.0 |
| 6. Jojoba oil | 10.0 |
| 7. Hybrid silicone composite powder*[4] | 3.0 |
| 8. Powder of Preparation Example 4 | 2.0 |

-continued

| (Components) | Weight (%) |
|---|---|
| 9. 1,3-Butylene glycol | 8.0 |
| 10. Glycine | 3.0 |
| 11. Sodium citrate | 0.2 |
| 12. Sodium chloride | 0.5 |
| 13. Antiseptic | q.s. |
| 14. Fragrance | q.s. |
| 15. Purified water | 56.8 |

*[1]KSG-340 (Shin-Etsu Chemical Co., Ltd., Japan)
*[2]KSG-44 (Shin-Etsu Chemical Co., Ltd., Japan)
*[3]KF-6038 (Shin-Etsu Chemical Co., Ltd., Japan)
*[4]KSP-100 (Shin-Etsu Chemical Co., Ltd., Japan)

(Preparation Process)

A: Components 1 to 8 were uniformly mixed together.

B: Components 9 to 13 and Component 15 were uniformly mixed together.

C: Under stirring conditions, B was slowly added and emulsified in A, followed by addition of Component 14 to give a W/O cream.

The resulting W/O cream was confirmed to be lightly spreadable without leaving squeakiness, be excellent in tight adhesion to the skin, be satisfactorily maintained on the skin, remain moist and fresh, give a light and refreshing feel upon use, be good in long-lasting quality, be free from temperature- or time-induced changes, and also be very excellent in usability and stability.

Example 17

Body Lotion

| (Components) | Weight (%) |
|---|---|
| 1. Alcohol | 17.0 |
| 2. 1,3-Butylene glycol | 3.0 |
| 3. Branched polyglycerine-modified silicone*[1] | 0.5 |
| 4. Glyceryl trioctanoate | 1.0 |
| 5. Powder of Preparation Example 5 | 2.0 |
| 6. Hybrid silicone composite powder*[2] | 10.0 |
| 7. Ammonium acryloyldimethyltaurate/VP copolymer | 0.4 |
| 8. Xanthan gum (2% aqueous solution) | 6.0 |
| 9. Sodium chloride | 0.1 |
| 10. Purified water | 60.0 |

*[1]KF-6100 (Shin-Etsu Chemical Co., Ltd., Japan)
*[2]KSP-100 (Shin-Etsu Chemical Co., Ltd., Japan)

(Preparation Process)

A: Components 1 to 6 were uniformly mixed together.

B: Components 7 to 10 were uniformly mixed together.

C: Under stirring conditions, A was slowly added and mixed into B to give a body lotion.

The resulting body lotion was confirmed to have a silky touch without stickiness or unctuousness, be lightly spreadable, remain moist and fresh, give a light and refreshing feel upon use, be free from temperature- or time-induced changes, and also be very excellent in usability and stability.

Example 18

Suncut Cream

| (Components) | Weight (%) |
|---|---|
| 1. Crosslinked polyether-modified silicone*[1] | 3.0 |
| 2. Crosslinked dimethylpolysiloxane*[2] | 2.0 |
| 3. Alkyl-modified branched polyether-modified silicone*[3] | 1.0 |
| 4. Neopentyl glycol dioctanoate | 5.0 |
| 5. Decamethylcyclopentasiloxane | 17.5 |
| 6. Octyl methoxycinnamate | 6.0 |
| 7. Acryl silicone resin (dissolved form)*[4] | 10.0 |
| 8. Caprylylsilane-treated fine particulate zinc oxide*[5] | 20.0 |
| 9. Powder of Preparation Example 4 | 3.0 |
| 10. 1,3-Butylene glycol | 2.0 |
| 11. Sodium citrate | 0.2 |
| 12. Sodium chloride | 0.5 |
| 13. Fragrance | q.s. |
| 14. Purified water | 29.8 |

*[1]KSG-240 (Shin-Etsu Chemical Co., Ltd., Japan)
*[2]KSG-15 (Shin-Etsu Chemical Co., Ltd., Japan)
*[3]KF-6038 (Shin-Etsu Chemical Co., Ltd., Japan)
*[4]KP-575 (Shin-Etsu Chemical Co., Ltd., Japan)
*[5]treated with AES-3083 (Shin-Etsu Chemical Co., Ltd., Japan)

(Preparation Process)

A: Component 7 was added to a portion of Component 5 and mixed to a uniform state, to which Components 8 and 9 were then added and dispersed with a bead mill.

B: Components 1 to 4, the remainder of Component 5, and Component 6 were uniformly mixed together.

C: Components 10 to 12 and Component 14 were mixed together to a uniform state.

D: C was added and emulsified in B, followed by addition of A and Component 12 to give a suncut cream.

The resulting suncut cream was confirmed to be evenly applicable over the skin because the applied area was slightly detectable, and also be very lightly spreadable without leaving stickiness, be excellent in tight adhesion to the skin, be satisfactorily maintained on the skin, give a light feel upon use without unctuousness, be good in water resistance, water repellency and sweat resistance, be very excellent in long-lasting quality, be less likely to cause make-up deterioration, and also be excellent in stability without temperature- or time-induced changes.

Example 19

Suncut Cream

| (Components) | Weight (%) |
|---|---|
| 1. Crosslinked polyether-modified silicone*[1] | 2.0 |
| 2. Crosslinked dimethylpolysiloxan*[2] | 3.0 |
| 3. Branched polyether-modified silicon*[3] | 1.5 |
| 4. Glyceryl trioctanoate | 3.5 |
| 5. Decamethylcyclopentasiloxane | 6.8 |
| 6. Dimethyl distearyl ammonium hectorite | 1.2 |
| 7. Titanium dioxide (dispersed form)*[4] | 20.0 |
| 8. Zinc oxide (dispersed form)*[5] | 15.0 |
| 9. Powder of Preparation Example 5 | 2.0 |
| 10. Branched polyglycerine-modified silicone*[6] | 0.5 |

-continued

| (Components) | Weight (%) |
|---|---|
| 11. 1,3-Butylene glycol | 5.0 |
| 12. Sodium citrate | 0.2 |
| 13. Sodium chloride | 0.5 |
| 14. Purified water | 38.8 |

*[1]KSG-210 (Shin-Etsu Chemical Co., Ltd., Japan)
*[2]KSG-15 (Shin-Etsu Chemical Co., Ltd., Japan)
*[3]KF-6028P (Shin-Etsu Chemical Co., Ltd., Japan)
*[4]SPD-T6 (Shin-Etsu Chemical Co., Ltd., Japan)
*[5]SPD-Z6 (Shin-Etsu Chemical Co., Ltd., Japan)
*[6]KF-6104 (Shin-Etsu Chemical Co., Ltd., Japan)

(Preparation Process)

A: Component 10 was dissolved in a portion of Component 5, and Component 9 was uniformly dispersed therein.

B: Components 1 to 4, the remainder of Component 5, Components 6 to 8 and A were uniformly mixed together.

C: Components 11 to 14 were mixed together.

D: C was added and emulsified in B to give a suncut cream.

The resulting suncut cream was confirmed to be evenly applicable, be lightly spreadable, be excellent in tight adhesion to the skin, leave no squeakiness, be satisfactorily maintained on the skin, give a light feel upon use without stickiness or unctuousness, be good in water resistance, water repellency and sweat resistance, be very excellent in long-lasting quality, be less likely to cause make-up deterioration, and also be excellent in stability without temperature- or time-induced changes.

Example 20

Pressed Cheek Color

| (Components) | Weight (%) |
|---|---|
| 1. Acryl silicone resin-treated mica*[1] | 12.0 |
| 2. Silicone-treated talc*[2] | 72.1 |
| 3. Red No. 202 | 0.3 |
| 4. Yellow iron oxide | 2.5 |
| 5. Black iron oxide | 0.3 |
| 6. Silicone-treated pigment-grade titanium dioxide*[2] | 0.5 |
| 7. Powder of Preparation Example 6 | 0.3 |
| 8. Phenyl-modified hybrid silicone composite powder*[3] | 2.0 |
| 9. Dimethylpolysiloxane (6 mm$^2$/second (25° C.)) | 5.0 |
| 10. Petrolatum | 2.0 |
| 11. Polyethylene wax | 3.0 |

*[1]treated with KP-574 (Shin-Etsu Chemical Co., Ltd., Japan)
*[2]KF-9909 (Shin-Etsu Chemical Co., Ltd., Japan)
*[3]KSP-300 (Shin-Etsu Chemical Co., Ltd., Japan)

(Preparation Process)

A: Components 1 to 8 were uniformly dispersed.

B: Components 9 to 11 were mixed together by heating.

C: B was added and uniformly mixed into A, and press-molded in a metal dish to give a pressed cheek color.

The resulting pressed cheek color was confirmed to be lightly spreadable without being too unctuous or powdery, leave no squeakiness, be excellent in adhesion to the skin, give a light feel upon use and remain moist, be good in water resistance, water repellency and sweat resistance, be good in long-lasting quality, be less likely to cause make-up deterioration, and also be excellent in stability without temperature- or time-induced changes.

Example 21

Loose Powder

| (Components) | Weight (%) |
|---|---|
| 1. Talc | balance |
| 2. Powder of Preparation Example 2 | 1.0 |
| 3. Amihope LL | 3.0 |
| 4. PMMA (10 μm)*[1] | 8.0 |
| 5. Antiseptic | q.s. |
| 6. Coloring material | q.s. |
| 7. Squalane | 1.0 |
| 8. Antiseptic | q.s. |
| 9. Antioxidant | q.s. |
| 10. Fragrance | q.s. |

*[1]Matsumoto Microsphere S-100 (Matsumoto Yushi-Seiyaku Co., Ltd., Japan)

(Preparation Process)

A: Components 1 to 7 were mixed together and pulverized.

B: A was transferred to a Henschel mixer, and Components 8 to 10 were added thereto, followed by stirring and mixing to a uniform state.

C: B was pulverized with an atomizer and then filled to give a loose powder.

The resulting loose powder was confirmed to be excellent in spreadability and smoothness upon application, and also be excellent in skin clarity after application to thereby give a natural finish with a bare skin appearance due to adequate covering power without causing white masking.

Example 22

Lipstick

| (Components) | Weight (%) |
|---|---|
| 1. Ceresin | 12.0 |
| 2. Carnauba wax | 1.0 |
| 3. Glyceryl 2-ethylhexanoate | 14.0 |
| 4. Mineral oil | 15.0 |
| 5. Hydrogenated polyisobutene | 20.0 |
| 6. Methylphenylpolysiloxane | 20.0 |
| 7. Octyldodecyl ricinoleate | 5.0 |
| 8. Red No. 202 | 1.0 |
| 9. Powder of Preparation Example 6 | 4.0 |
| 10. Titanated mica | 3.0 |
| 11. Antioxidant | q.s. |
| 12. Antiseptic | q.s. |

(Preparation Process)

A: Components 1 to 12 were mixed together by heating and uniformly stirred.

B: After A was defoamed, the bulk was poured into a mold and quickly cooled to give a lipstick.

The resulting lipstick was confirmed to have an excellent luster, ensure tight adhesion to the lip, and retain adequate spreadability. Moreover, the lipstick obtained in this example was also confirmed to ensure the same color before and after application, although it is difficult to obtain the same color tone before and after application in products comprising commonly-used pigment-grade titanium dioxide.

Example 23

Lip Color

| (Components) | Weight (%) |
|---|---|
| 1. Dextrin palmitate | 8.0 |
| 2. Glyceryl 2-ethylhexanoate | 14.0 |
| 3. Methylphenylpolysiloxane | balance |
| 4. Octyldodecyl ricinoleate | 15.0 |
| 5. Hydrogenated polyisobutene | 20.0 |
| 6. Mineral oil | 30.0 |
| 7. Red No. 202 | 0.1 |
| 8. Titanated mica | 1.0 |
| 9. Powder of Preparation Example 3 | 0.5 |
| 10. Antiseptic | q.s. |
| 11. Antioxidant | q.s. |

(Preparation Process)

A: Components 1 to 11 were mixed together by heating and uniformly stirred.

B: After defoaming, A was filled into an appropriate container and then slowly cooled to room temperature to give a lip color.

The resulting lip color was confirmed to have an excellent luster, ensure an adequate thickness, and be excellent in tight adhesion to the lip. Moreover, the lip color obtained in this example was also confirmed to ensure the same color before and after application, although it is difficult to obtain the same color tone before and after application in products comprising commonly-used pigment-grade titanium dioxide.

Example 24

Lip Gloss

| (Components) | Weight (%) |
|---|---|
| 1. Dextrin palmitate | 10.0 |
| 2. Diisostearyl malate | 45.0 |
| 3. Liquid paraffin (500 cs) | 43.6 |
| 4. Antiseptic | 0.1 |
| 5. Antioxidant | 0.1 |
| 6. Titanated mica | 0.1 |
| 7. Aluminum powder | 0.1 |
| 8. Powder of Preparation Example 5 | 1.0 |

(Preparation Process)

A: Components 1 to 5 were uniformly dissolved by heating at 85° C.

B: Components 6 to 8 were added and uniformly dispersed in A.

C: The dispersion was filled into a container at the elevated temperature and quickly cooled to room temperature to give a lip gloss.

The resulting lip gloss was confirmed to be excellent in tight adhesion to the lip and stability over time, and ensure the same color before and after application.

Example 25

Eyeliner

| (Components) | Weight (%) |
|---|---|
| 1. Black iron oxide | 7.0 |
| 2. Powder of Preparation Example 1 | 5.0 |
| 3. Vinyl acetate resin emulsion | 45.0 |
| 4. Concentrated glycerin | 6.0 |
| 5. POE(20) sorbitan laurate | 1.8 |
| 6. Carboxymethylcellulose (10% aqueous solution) | 18.0 |
| 7. Purified water | 14.9 |
| 8. Antiseptic | 0.1 |
| 9. Fragrance | 0.2 |

(Preparation Process)

A: Components 5 and 6 were added to Component 7, to which Components 1 to 3 were then added and treated in a colloid mill.

B: Components 4, 8 and 9 were mixed together, to which A was then added at 70° C. and uniformly dispersed. The dispersion was cooled and filled to give an eyeliner.

The resulting eyeliner was confirmed to be excellent in tight adhesion to the skin, long-lasting quality, and color tone.

Example 26

Mascara

| (Components) | Weight (%) |
|---|---|
| 1. Water | 26.0 |
| 2. Polyvinylpyrrolidone | 2.0 |
| 3. Butylene glycol | 2.0 |
| 4. Cationated cellulose (1% aqueous solution) | 10.0 |
| 5. Bentonite | 0.5 |
| 6. Triethanolamine | 1.7 |
| 7. Talc | 2.7 |
| 8. Powder of Preparation Example 5 | 1.0 |
| 9. Yellow iron oxide | 0.9 |
| 10. Red iron oxide | 0.9 |
| 11. Black iron oxide | 4.8 |
| 12. Carnauba wax | 5.5 |
| 13. Beeswax | 9.0 |
| 14. Stearic acid | 2.0 |
| 15. Self-emulsifiable glyceryl stearate | 2.0 |
| 16. Propylene glycol stearate | 2.0 |
| 17. Hydrogenated polyisobutene | 2.0 |
| 18. Cyclomethicone | 4.0 |
| 19. Antiseptic | q.s. |
| 20. Antioxidant | q.s. |
| 21. Resin emulsion | 20.0 |

(Preparation Process)

A: Components 7 to 11 were stirred and mixed together in a Henschel mixer.

B: A was added to Components 1 to 6 and uniformly dispersed with a stirrer.

C: In another container, Components 12 to 20 were dissolved by heating.

D: C was added and emulsified in B, and then cooled to 40° C., followed by addition of Component 21. The mixture was cooled to room temperature to give a mascara.

The resulting mascara was confirmed to have an adequate luster and be excellent in adhesion to eyelashes, long-lasting quality, and color tone.

Example 27

Cream Eyeshadow

| (Components) | Weight (%) |
|---|---|
| 1. Acryl silicone resin (dissolved form)*[1] | 10.0 |
| 2. Stearyl-modified acryl silicone resin*[2] | 2.0 |
| 3. Branched polyether-modified silicon*[3] | 1.5 |
| 4. Decamethylcyclopentasiloxane | 20.3 |
| 5. Isotridecyl isononanoate | 3.0 |
| 6. Dimethyl distearyl ammonium hectorite | 1.2 |
| 7. Acryl silicone resin-treated pigment*[4] | 10.0 |
| 8. Powder of Preparation Example 4 | 10.0 |
| 9. Spherical nylon | 3.0 |
| 10. Talc | 4.0 |
| 11. Ethanol | 5.0 |
| 12. Purified water | 30.0 |

*[1]KP-545 (Shin-Etsu Chemical Co., Ltd., Japan)
*[2]KP-561P (Shin-Etsu Chemical Co., Ltd., Japan)
*[3]KF-6028P (Shin-Etsu Chemical Co., Ltd., Japan)
*[4]treated with KP-574 (Shin-Etsu Chemical Co., Ltd., Japan)

(Preparation Process)
A: Components 1 to 6 were mixed together, to which Components 7 to 10 were then added, and uniformly mixed and dispersed.
B: Components 11 to 12 were mixed together.
C: B was added and emulsified in A to give a cream eyeshadow.

The cream eyeshadow thus obtained was confirmed to be lightly spreadable without being too unctuous or powdery, leave no squeakiness, be excellent in adhesion to the skin, give a light feel upon use and remain moist, be good in water resistance, water repellency and sweat resistance, be good in long-lasting quality, less likely to cause make-up deterioration, and also be excellent in stability without temperature- or time-induced changes.

Example 28

Eyeshadow

| (Components) | Weight (%) |
|---|---|
| 1. Methicone-treated talc | 36.5 |
| 2. Powder of Preparation Example 2 | 9.0 |
| 3. Boron nitride | 9.0 |
| 4. Titanated mica | 35.0 |
| 5. Dimethicone 1000 cs | 5.0 |
| 6. Red No. 202 | 0.5 |
| 7. Neopentyl glycol dioctanoate | 1.0 |
| 8. Squalane | 4.0 |
| 9. Antiseptic | q.s. |
| 10. Antioxidant | q.s. |

(Preparation Process)
A: Components 1 to 5 were mixed together and pulverized.
B: A was transferred to a Henschel mixer, and Components 6 to 10, which had been mixed separately, were added thereto, followed by stirring and mixing to a uniform state.
C: B was pulverized with an atomizer and press-molded in an aluminum dish to give an eyeshadow.

The resulting eyeshadow was confirmed to be excellent in long-lasting quality, tight adhesion to the skin, color tone, and usability.

Example 29

Nail Enamel

| (Components) | Weight (%) |
|---|---|
| 1. Nitrocellulose (½ seconds) | 10.0 |
| 2. Modified alkyd resin | 10.0 |
| 3. Acetyl tributyl citrate | 5.0 |
| 4. Butyl acetate | 15.0 |
| 5. Ethyl acetate | 20.0 |
| 6. Ethanol | 5.0 |
| 7. Toluene | 35.0 |
| 8. Ultramarine blue | 0.5 |
| 9. Powder of Preparation Example 4 | 0.1 |
| 10. Organo-modified montmorillonite | 1.0 |

(Preparation Process)
A: Components 8 and 9 were dissolved in a portion of Components 2 and 3 and then kneaded well.
B: To A, the remainder of Components 2 and 3, as well as Components 1, 4 to 7 and 10 were added and mixed, and the mixture was then filled into a container to give a nail enamel.

The resulting nail enamel was confirmed to be excellent in tight adhesion to the nail, stability over time, and color tone.

Example 30

Polyhydric Alcohol-in-oil Type Emulsified Solid Cheek Color

| (Components) | Weight (%) |
|---|---|
| 1. Crosslinked polyglycerine-modified silicone*[1] | 3.0 |
| 2. Crosslinked dimethylpolysiloxan*[2] | 5.0 |
| 3. Decamethylcyclopentasiloxane | 18.0 |
| 4. Dimethylpolysiloxane (6 mm$^2$/second (25° C.)) | 21.6 |
| 5. Cetyl isooctanoate | 5.0 |
| 6. Behenyl-modified acryl silicone resin*[2] | 3.0 |
| 7. Paraffin wax (melting point: 80° C.) | 9.0 |
| 8. Dimethyl distearyl ammonium hectorite | 0.2 |
| 9. Powder of Preparation Example 6 | 10.0 |
| 10. Acryl silicone-treated blue 401*[3] | 5.0 |
| 11. Acryl silicone-treated black iron oxid*[3] | 0.2 |
| 12. Acryl silicone-treated mica*[3] | 5.0 |
| 13. Antiseptic | q.s. |
| 14. Fragrance | q.s. |
| 15. 1,3-Butylene glycol | 15.0 |

*[1]KSG-710 (Shin-Etsu Chemical Co., Ltd., Japan)
*[2]KSG-15 (Shin-Etsu Chemical Co., Ltd., Japan)
*[3]KP-562P (Shin-Etsu Chemical Co., Ltd., Japan)

(Preparation Process)
A: Components 1 to 8 were uniformly mixed together by heating at 80° C.
B: Components 9 to 12 were uniformly mixed together and added to A, followed by dispersion to a uniform state.
C: Components 13 and 15 were mixed together and heated to 80° C.
D: C was added and emulsified in B, and Component 14 was added thereto. The emulsion was poured into a metal dish and cooled to give a polyhydric alcohol-in-oil type emulsified solid cheek color.

The resulting polyhydric alcohol-in-oil type emulsified solid cheek color was confirmed to be a non-aqueous polyhydric alcohol-in-oil type emulsified solid cheek color, which was lightly spreadable, left no stickiness or unctuousness, was excellent in adhesion to the skin, kept the skin moist without causing white masking, and was highly stable over time.

Example 31

Cheek Color

| (Components) | Weight (%) |
|---|---|
| 1. Talc | balance |
| 2. Sericite | 60.9 |
| 3. Fine particulate titanium dioxide | 3.0 |
| 4. Powder of Preparation Example 3 | 2.0 |
| 5. Coloring material | q.s. |
| 6. Octyl methoxycinnamate | 3.0 |
| 7. Octyl palmitate | 5.0 |
| 8. Antiseptic | q.s. |
| 9. Antioxidant | q.s. |

(Preparation Process)
A: Components 6 to 9 were dissolved by heating.
B: Components 1 to 5 were mixed together in a Henschel mixer, and A was mixed thereinto.
C: B was pulverized with an atomizer and molded in an inner dish to give a cheek color.

The resulting cheek color was confirmed to be excellent in spreadability and smoothness upon application, and give a natural finish ensuring the same color before and after application.

Example 32

Cream-based Lipstick

| (Components) | Weight (%) |
|---|---|
| 1. Dextrin palmitate/ethylhexanoate*[1] | 9.0 |
| 2. Polyglyceryl-2 triisostearate | 10.0 |
| 3. Glyceryl trioctanoate | 8.0 |
| 4. Alkyl-modified crosslinked dimethylpolysiloxane*[2] | 8.0 |
| 5. Alkyl-modified branched polyglycerine-modified silicon*[3] | 2.0 |
| 6. Decamethylcyclopentasiloxane | 40.0 |
| 7. 1,3-Butylene glycol | 5.0 |
| 8. Purified water | 18.0 |
| 9. Red No. 201 | q.s. |
| 10. Red No. 226 | q.s. |
| 11. Yellow No. 4 | q.s. |
| 12. Powder of Preparation Example 2 | q.s. |
| 13. Mica | q.s. |
| 14. Fragrance | q.s. |

*[1]Leopard TT (Chiba Flour Milling, Japan)
*[2]KSG-43 (Shin-Etsu Chemical Co., Ltd., Japan)
*[3]KF-6105 (Shin-Etsu Chemical Co., Ltd., Japan)

(Preparation Process)
A: A portion of Component 2 was mixed with Components 9 to 12 and dispersed by a roller.
B: Component 1, the remainder of Component 2 and Components 3 to 6 were heated and uniformly mixed together.
C: A was added and uniformly mixed into B.
D: Components 7 and 8 were mixed together and heated, and then added and emulsified in C.
E: Components 13 and 14 were added to D to give a cream-based lipstick.

The resulting cream-based lipstick was confirmed to be lightly and easily spreadable over the lip, leave no stickiness or unctuousness, remain moist and keep the lip from feeling dry, be good in long-lasting quality without causing white masking or blotting, and also be highly stable over time.

Example 33

Facial Cleansing Foam

| (Components) | Weight (%) |
|---|---|
| 1. Lauric acid | 3.0 |
| 2. Myristic acid | 9.0 |
| 3. Palmitic acid | 8.0 |
| 4. Stearic acid | 10.0 |
| 5. Glycerine | 15.0 |
| 6. 1,3-Butylene glycol | 7.0 |
| 7. Glyceryl stearate | 1.5 |
| 8. Antiseptic | 0.2 |
| 9. Chelating agent | 0.1 |
| 10. Water | balance |
| 11. Potassium hydroxide | 6.0 |
| 12. Cocamidopropyl betaine | 3.3 |
| 13. Potassium cocoyl glycinate | 3.0 |
| 14. Glycosyl trehalose | 4.5 |
| 15. Powder of Preparation Example 3 | 1.5 |

(Preparation Process)
A: Components 1 to 9 were mixed together and dissolved by heating.
B: Components 10 and 11 were weighed in another container and added to A, followed by saponification.
C: Components 12 to 15 were added to B, uniformly stirred and mixed, and then cooled to room temperature. The mixture was then filled into an appropriate container to give a facial cleansing foam.

The resulting facial cleansing foam was confirmed to have a clear white appearance, and be excellent in foaming quality and foam-holding quality without impairing washing properties.

Examples 34 to 37

External Additive for Toner

A water suspension containing the cocoon-shaped rutile-type titanium dioxide of Preparation Example 1 was warmed and maintained at 35° C., and adjusted to pH 1.2 by addition of 8N aqueous sodium hydroxide while stirring. After addition of 40% by weight of n-hexyltrimethoxysilane, the mixture was continued to be stirred for 30 minutes and neutralized to pH 6.5 by addition of 8N aqueous sodium hydroxide, followed by filtration and washing with water. The filtered and washed cake was dried at 150° C. and then finely pulverized in an air jet mill.

(Measurement of Hydrophobicity)
Aqueous solutions containing methanol in increments of 2.5% by mass were prepared in test tubes, and a small amount of the hydrophobically treated fine powder was introduced thereinto. Each test tube was observed for the presence or absence of sedimentation. The hydrophobicity (%) was expressed as the % by mass range within which sedimentation was observed.

The hydrophobically treated fine powder of Example 34 had a hydrophobicity of 57.5% to 60.0%, which was sufficient to give a hydrophobic titanium dioxide available for use as an external additive for toner.

Example 35

A water suspension containing the cocoon-shaped rutile-type titanium dioxide of Preparation Example 2 was adjusted to pH 6.5 at 70° C., and 7.0% by mass of sodium stearate was added thereto. The mixture was continued to be stirred for 1 hour, and then filtered and washed with water. The filtered and washed cake was dried at 150° C. and then finely pulverized in an air jet mill. This fine powder had a hydrophobicity of 55.0% to 57.5%, which was sufficient to give a hydrophobic titanium dioxide available for use as an external additive for toner.

Example 36

A water suspension containing the cocoon-shaped rutile-type titanium dioxide obtained in Example 6 was neutralized to pH 6.5 by addition of 8N aqueous sodium hydroxide, and then filtered and washed with water. The filtered and washed cake was dried at 130° C. and finely pulverized in an air jet mill. The finely pulverized cocoon-shaped rutile-type titanium dioxide was treated with 30% by weight of i-butyltrimethoxysilane in a Henschel mixer under dry conditions, and then pulverized in a micropulverizer. This fine powder had a hydrophobicity of 52.5% to 55.0%, which was sufficient to give a hydrophobic titanium dioxide available for use as an external additive for toner.

Example 37

A water suspension containing the cocoon-shaped rutile-type titanium dioxide obtained in Example 3 was neutralized to pH 6.5 by addition of 8N aqueous sodium hydroxide, and then filtered and washed with water. The filtered and washed cake was dried at 130° C. and finely pulverized in an air jet mill. The finely pulverized cocoon-shaped rutile-type titanium dioxide was treated with 30% by weight of polydimethylsiloxane in a Henschel mixer under dry conditions, and then pulverized in a micropulverizer. This fine powder had a hydrophobicity of 65.0% to 67.5%, which was sufficient to give a hydrophobic titanium dioxide available for use as an external additive for toner.

What is claimed is:

1. Cocoon-shaped rutile-type titanium dioxide having a specific surface area of 120 to 180 m²/g in the form of oriented and aggregated rod-shaped particles, having a major axial plane and a minor axial direction, in which the major axial planes of rod-shaped particles each having a minor axial diameter of 3 to 10 nm are oriented and aggregated in the minor axial direction, wherein the oriented and aggregated particles have an apparent mean major axial length of 80 to 300 nm, an apparent mean minor axial length of 30 to 150 nm, and an apparent mean axial ratio (apparent mean major axial length/apparent mean minor axial length) of 1.1 to 4, and wherein both major axial ends of the oriented and aggregated particles are round- or elliptical-shaped.

2. The cocoon-shaped rutile-type titanium dioxide according to claim 1, wherein the particle surface is coated with a layer containing one or more inorganic or organic materials.

3. The cocoon-shaped rutile-type titanium dioxide according to claim 2, wherein the inorganic material coated over the particle surface comprises a hydroxide or oxide of one or more members selected from the group consisting of aluminum, silicon, zinc, titanium, zirconium, iron, cerium and tin.

4. The cocoon-shaped rutile-type titanium dioxide according to claim 2, wherein the organic material coated over the particle surface comprises silicone-based compounds.

5. A cosmetic comprising the cocoon-shaped rutile-type titanium dioxide according to claim 1.

6. An external additive for toner comprising the cocoon-shaped rutile-type titanium dioxide according to claim 1, wherein the titanium dioxide is hydrophobically treated.

7. The cosmetic of claim 5, wherein the particle surface of the cocoon-shaped rutile-type titanium dioxide is coated with a layer containing one or more inorganic or organic materials.

8. The cosmetic of claim 7, wherein the inorganic material coated over the particle surface comprises a hydroxide or oxide of one or more members selected from the group consisting of aluminum, silicon, zinc, titanium, zirconium, iron, cerium and tin.

9. The cosmetic of claim 7, wherein the organic material coated over the particle surface comprises silicone-based compounds.

10. The external additive for toner of claim 6, wherein the particle surface of the cocoon-shaped rutile-type titanium dioxide is coated with a layer containing one or more inorganic or organic materials.

11. The external additive for toner of claim 10, wherein the inorganic material coated over the particle surface comprises a hydroxide or oxide of one or more members selected from the group consisting of aluminum, silicon, zinc, titanium, zirconium, iron, cerium and tin.

12. The external additive for toner of claim 10, wherein the organic material coated over the particle surface comprises one or more members selected from the group consisting of silicone-based compounds, coupling agents and fatty acids.

13. The cocoon-shaped rutile-type titanium dioxide according to claim 2, wherein the organic material coated over the particle surface comprises coupling agents.

14. The cocoon-shaped rutile-type titanium dioxide according to claim 2, wherein the organic material coated over the particle surface comprises fatty acids.

15. The cosmetic of claim 7, wherein the organic material coated over the particle surface comprises coupling agents.

16. The cosmetic of claim 7, wherein the organic material coated over the particle surface comprises fatty acids.

* * * * *